(12) United States Patent
Bergelin et al.

(10) Patent No.: US 10,206,604 B2
(45) Date of Patent: *Feb. 19, 2019

(54) ARRANGEMENT FOR FACILITATING WOUND HEALING, A METHOD FOR MEASURING WOUND HEALING AND A WOUND DRESSING

(71) Applicants: Åbo Akademi, Turku (FI); Tampereen teknillinen yliopisto, Tampere (FI)

(72) Inventors: Mikael Bergelin, Turku (FI); Jan-Erik Eriksson, Turku (FI); Max Johansson, Turku (FI); Chunlin Xu, Turku (FI); Ann-Sofie Leppänen, Turku (FI); Stefan Willför, Turku (FI); Simo Köppä, Tampere (FI); Atte Kekonen, Tampere (FI); Heimo O. Ylänen, Tampere (FI); Jari Viik, Tampere (FI); Jari Hytti, Tampere (FI)

(73) Assignee: CutoSense Oy, Turku (FI)

( * ) Notice: Subject to any disclaimer, the term of this patent is extended or adjusted under 35 U.S.C. 154(b) by 307 days.

This patent is subject to a terminal disclaimer.

(21) Appl. No.: 14/960,340

(22) Filed: Dec. 5, 2015

(65) Prior Publication Data
US 2016/0081580 A1    Mar. 24, 2016

Related U.S. Application Data

(63) Continuation-in-part of application No. 14/893,084, filed as application No. PCT/FI2014/050388 on May 21, 2014.

(30) Foreign Application Priority Data

May 23, 2013 (FI) .................................... 20135557

(51) Int. Cl.
*A61N 1/20* (2006.01)
*A61B 5/053* (2006.01)
(Continued)

(52) U.S. Cl.
CPC ............ *A61B 5/0531* (2013.01); *A61B 5/445* (2013.01); *A61N 1/0468* (2013.01); *A61N 1/0476* (2013.01); *A61N 1/36014* (2013.01)

(58) Field of Classification Search
CPC .... A61N 1/205; A61N 1/0468; A61N 1/0476; A61N 1/0484; A61N 1/0496;
(Continued)

(56) References Cited

U.S. PATENT DOCUMENTS

2006/0182788 A1* 8/2006 Singh .................. A61K 9/7061
424/448
2006/0270942 A1* 11/2006 McAdams ........... A61B 5/0531
600/547

(Continued)

FOREIGN PATENT DOCUMENTS

WO    WO 2004049937    6/2004
WO    WO 2006081497    8/2006
(Continued)

OTHER PUBLICATIONS

Claims of U.S. Appl. No. 14/893,084, filed Nov. 23, 2015.*

*Primary Examiner* — Michael Carey
(74) *Attorney, Agent, or Firm* — Seppo Laine Oy

(57) ABSTRACT

The present invention relates to the field of electrotherapy and measuring by means of electric cur-rents for diagnostic purposes, and more particularly to an electrode arrangement for facilitating wound healing, a method for measuring wound healing and a wound dressing having an electrode arrangement. A wound dressing according is described which includes at least two impedance reference electrodes, (Continued)

a frame like counter-electrode and stimulation electrodes in a form of an array; and a bioadhesive affinity layer surrounding the stimulation electrodes; said wound dressing being suited for applying on top of the wound so that the stimulation electrode array is on the wound area, and that the at least two impedance reference electrodes and the frame like counter-electrode are suited for placing in contact with the healthy skin surrounding the wound area; which electrodes, are suited for applying LIDC type electrical stimulation current to the wound area and for bioimpedance measurement.

14 Claims, 8 Drawing Sheets

(51) Int. Cl.
*A61N 1/04* (2006.01)
*A61B 5/00* (2006.01)
*A61N 1/36* (2006.01)

(58) Field of Classification Search
CPC .. A61N 1/36014; A61B 5/053; A61B 5/0531; A61B 5/445; A61B 5/4848; A61F 13/0253
USPC .................................. 607/50; 600/301, 300
See application file for complete search history.

(56) References Cited

U.S. PATENT DOCUMENTS

2008/0103550 A1    5/2008  Wenzel et al.
2011/0015697 A1*  1/2011  McAdams ............. A61B 5/445
                                               607/50

FOREIGN PATENT DOCUMENTS

| WO | WO 2008013936 A1 | 1/2008 |
|----|------------------|--------|
| WO | WO 2009092616    | 7/2009 |
| WO | WO 2009144615    | 12/2009 |
| WO | WO 2011004165 A1 | 1/2011 |

* cited by examiner

ARRANGEMENT FOR FACILITATING WOUND HEALING, A METHOD FOR MEASURING WOUND HEALING AND A WOUND DRESSING

FIELD OF THE INVENTION

The present invention relates generally to the field of electrotherapy and measuring by means of electric currents for diagnostic purposes, and more particularly to an electrode arrangement for facilitating wound healing, a method for measuring wound healing and a wound dressing having an electrode arrangement.

BACKGROUND OF THE INVENTION

Wounds such as e.g. chronic wounds and ulcers affect nearly 1% of population and up to 10% of institutionalized patients. By the year 2030, 366 million people worldwide are estimated to suffer from diabetes further increasing the prevalence of chronic wounds and ulcers.

Aging population in the western world and increase in the prevalence of various diseases exposing to chronic wounds, such as diabetes and vascular diseases, have made it ever more important to develop novel therapeutic methods and further improve the existing therapeutic methods for non-healing ulcers. Social problems for an individual patient are enormous and the financial burden to the healthcare system is huge due to costly treatment of chronic wounds and the related indirect costs. To further underline the prevalent problem of chronic wounds and ulcers, in addition to increased mortality, approximately 80% of leg amputations are due to chronic vascular ulcers.

Lower extremity wounds of venous origin are commonly riddled with peripheral edema. This is due to vascular insufficiency; incompetence and dysfunction of veins and valves to transport blood in a normal way. This results in accumulation of highly conductive fluid into the interstitial space of the affected limb.

Edema prevents appropriate transport of oxygen and nutrients, which is essential for proper wound healing to occur. Edema also adds the mechanical stress in the wound site and disturbs waste removal from the wound area. A commonly used method to ease edema is compression therapy. Compression stockings are used for improving healing of chronic wounds of vascular etiology.

In summary, conventional treatment of chronic wounds and ulcers has so far been mainly passive; firstly to remove or control the impediments for healing and secondly to cover the wound area with an occlusive dressing to allow nature to take its course.

A finding in the wound care practices was that a moist environment is beneficial to the non-healing wound and that the occlusive dressings do not increase the risk for infection. This may partly relate to the improved ion transport and improved function of endogenous electric fields. Therefore, an ideal dressing for a chronic ulcer would provide a moist environment, absorb exudates, prevent the maceration of surrounding tissue and would be long term and cost effective. For wounds and ulcers that fail to heal, the treatment in the end often leads to surgical debridement under anaesthesia.

Recent studies suggest that endogenous electrical fields generated immediately after skin break may work as an initiating force for wound healing. This is due to instant collapse of transepithelial potential (TEP) in the wound area and resulting short circuit and flow of ionic current. As the wound heals the integrity of skin is gradually regained and eventually TEP is resumed.

Therefore, in order to improve the healing rate, a therapeutic approach which utilizes electrical stimulation of the wound via application of direct current should be beneficial. In a typical electrical stimulation of the wound low current and low voltage direct current is applied to the surface of the wound in order to stimulate the healing of the wound.

The electrical stimulation of the wound has been found to affect the biological healing of the wound in the inflammation phase of the wound, in the proliferation phase of the wound and in the epithelisation phase of the wound. In the inflammation phase of the wound the electrical stimulation of the wound initiates the wound healing process, increases the blood circulation, promotes phagocytosis, improves tissue oxygen intake, reduces edema, stimulates fibroblasts and epithelial cells, stimulates DNA synthesis, calms the infection and dissolves the necrotic tissue. In the proliferation phase of the wound the electrical stimulation of the wound stimulates fibroblasts and epithelial cells, stimulates DNA synthesis and protein synthesis, adenosine triphosphate (ATP) formation, enhances membrane transport and stimulates the diminishing of the wound. In the epithelisation phase of the wound the electrical stimulation of the wound stimulates the reformation and the migration of the epithelial cells and leads to softer and thinner skin, and improved scarring. Higher quality scarring is a factor in decreasing the high recurring tendency of a chronic wound.

Vascularization plays a role in soft tissue healing, and hence enhancing angiogenesis to ensure sufficient blood flow in the newly formed epithelial layer will support the healing process. Vascular endothelial growth factor (VEGF) has been successfully used in preclinical ischaemic tissue models to enhance and promote the development of collateral blood vessels. Also, dissolution of certain bioactive glass compositions have been shown to stimulate release of angiogenetic growth factors resulting in an in-crease in tubule branching and formation of complex networks of interconnected tubules. Soluble products of these bioactive glasses induce endothelial cell proliferation and up-regulation of VEGF production, which indicate that these glasses possess a proangiogenic potential. Significantly enhanced mitogenic stimulation of endothelial cells with an additive effect with VEGF release has also been observed in the presence of a BAG coating.

It has been shown that the applying of electrical stimulation in the form of low intensity direct current (LIDC) to the wound has caused the wound to heal drastically faster and at a wider area. The faster healing of the chronic wounds and ulcers brings substantial savings both in terms of financial costs and human suffering. Chronic wounds are a cause for disability, pain, emotional and social problems for the patients. Chronic wounds are associated with prolonged hospitalizations and considerable morbidity. These wounds, also known as ulcers, represent a major burden for the healthcare system affecting a large population of patients. Chronic wounds persist for months or even years representing medical, social, and economic problems for individuals and the society.

There are some prior art accelerating wound healing products in the market available as consumer products. However, the functionality of these prior art wound healing products is very limited as their principle of operation is based on a large number of independent miniature galvanic cells that are in contact with the wound area. Although this allows for easy adjustment of dressing size, the lack of possibility for controlling the current-flow, both in terms of magnitude and direction, is expected to diminish the effect of this therapy. The problem is that the stimulus current generated by this type of prior art electrode array does not penetrate into the actual wound tissue, but rather mainly flows along the wound surface which severely limits the accelerating effect on the healing process.

Furthermore, one major problem in wound care is associated with monitoring of the healing process. Today, the assessment of progress of chronic wound healing is generally based on visual investigation by photographing and monitoring the size and the colour of the wound. Visual assessment is always influenced by a certain degree of subjectivity. Sometimes ultrasound is used for imaging the structure of the wound; also laboratory tests of exudate samples or biopsied tissue are done. These methods are fairly laborious and cannot be applied for daily assessment of wound healing. All these methods require disturbing the wound by removal of the wound dressing and visual inspection of the wound area to assess the onset of formation of granulation tissue and to ensure that the wound is not becoming infected.

There are some prior art wound monitoring sensors available, e.g. array sensors which take the form of patterns on insulating material. However, these prior art wound monitoring sensors may typically use materials that interfere with or irritate the wound, occlude the wound and can cause skin maceration. Also, some of the prior art wound monitoring sensors adhere to the wound, which can result in wound damage when they are removed. Furthermore, some of the prior art wound monitoring sensors also interfere with the healing of the wound by interfering with moisture control, whilst some only have a limited lifetime in a wound environment.

As the bioimpedance measurement utilizes low level AC excitation current, it does not possess any risks or inconvenience for the patient. The idea of utilizing bioimpedance monitoring of a chronic wound is based on the pathophysiology of the wound. Often the integrity of the skin is lost in chronic wounds, and from an electrical point of view, the loss of high impedance stratum corneum leads into steep decrease in measured impedance. As the healing of the wound proceeds, the wound base lifts up and the wound starts to close up from the peripherals. Finally, the skin integrity is obtained. The gradual gain in the skin integrity is observed as increasing impedance particularly at lower frequencies.

Generally speaking, a chronic wound is trapped in an on-going inflammation phase of the wound healing process. Prolonged inflammation of a chronic wound is characterized by accumulation of highly conductive fluid into the wound and the surrounding area. The fluids may accumulate into the intracellular space as a result of ischemia. If the blood flow to the tissues is interrupted, cell metabolism continues but in an anaerobic way. However, a prolonged ischemia inevitably results in decline of metabolism. This results in the decreased activity of ion pumps, which leads changes in the ion distribution in extracellular fluid and intracellular fluid. The result is cellular edema because of inflow of water and sodium into the cell. The decline of extracellular fluid volume reduces the width of the electrical path of the low frequency current and increases the extracellular resistance. Severe ischemia finally results in cell necrosis. The cellular integrity is lost in necrosis and intracellular fluid leaks into the extracellular space. The necrosis is observed as a decrease in extracellular resistance.

The fluids in a chronic wound may also accumulate into extracellular space. The increased volume of extracellular fluid can be observed as a decrease in the extracellular resistance. Often related to the chronic wounds, the swelling is due to increased vasodilatation and increased permeability of the capillaries. As a result of this the fluid accumulates into the extracellular space. Another possible cause for fluid accumulation is peripheral edema. Peripheral edema results from increased capillary permeability or impaired return of fluid by lymphatic system from the interstitial space to vascular compartment. Lymphedema is a result of impaired function of lymphatic system and the fluid tends to accumulate into the extracellular space.

European patent specification EP 1569553B1 presents a prior art wound mapping system presenting an array of rectangular electrodes that may be used to stimulate wound tissue electrically or measure impedance of wound tissue. The measurement electrodes are isolated from each other by a non-conducting hydrogel layer. In use, the conducting parts of the stimulating electrodes are in direct contact with wound tissue via a hydrogel patch on the exposed conducting electrode. The conducting parts of the stimulating electrodes are designed to be electrically connected to the tissue but not to measure moisture above the wound or at a localised site between the electrodes. However, this allows the electrodes to dry into healing tissue and stick to the healed cell layer. Removal of the device with the wound dressing would remove the healed skin. Application of a hydrogel to the electrodes in contact with the wound area does little to alleviate the problem as it will dry out before removal of the dressing. Development of a tool that would allow objective online monitoring without disturbance would be of great importance.

Conventional prior art wound dressings and prior art electrode arrangements for facilitating wound healing have many problems and disadvantages. Regardless of the massive effort put into and improvements obtained in the area of the treatment of chronic wounds, many chronic wounds still remain non-responsive to the conventional treatment and a need to further develop the existing and new therapeutic methods is obvious. Furthermore, the need for continuous, non-invasive and objective solution for monitoring chronic wound healing without disturbing the delicate healing process is also obvious.

As mentioned above, there are a lot of deficiencies in the current wound dressings and electrode arrangements for facilitating wound healing. There is a clear demand in the market for a new type of an electrode arrangement for facilitating wound healing that would be better and more efficient than the current prior art electrode arrangement solutions. Likewise, there is a clear demand in the market for a new type of a wound dressing having a wound healing electrode arrangement that would be better and more efficient than the current prior art wound dressing solutions.

SUMMARY OF THE INVENTION

An object of an embodiment of the present invention is thus to provide an electrode arrangement for facilitating wound healing and a wound dressing having an electrode arrangement so as to overcome the above mentioned problems and to alleviate the above mentioned disadvantages.

Described herein is an arrangement for facilitating wound healing, which arrangement comprises at least two impedance reference electrodes, a frame like counter-electrode and stimulation electrodes in a form of an array; and a bioadhesive affinity layer surrounding the stimulation electrodes;

said arrangement being suited for applying on top of the wound so that the stimulation electrode array is on the wound area, and that the at least two impedance reference electrodes and the frame like counter-electrode are suited for placing in contact with the healthy skin surrounding the wound area; which electrodes are suited for applying LIDC type electrical stimulation current to the wound area and for bioimpedance measurement.

According to an example, in the arrangement, the frame like counter-electrode is anode electrode and the stimulation electrodes are cathode electrodes, or vice versa. According to an example, in the arrangement, the electrodes are suited for bioimpedance measurement with measurement frequencies in the range of 10 Hz-200 000 Hz, According to an example, in the range of 1 000 Hz-50 000 Hz.

According to an example, in the electrode arrangement, the polarity of the frame like counter-electrode and the stimulation electrodes is switchable. According to an example, in the electrode arrangement, the electrodes are multiplexed.

Furthermore, the objects of the invention are achieved by a method for measuring wound healing, which method comprises
 applying LIDC type electrical stimulation current to the wound area with the help of a frame like counter-electrode and stimulation electrodes in a form of an array, and
 performing bioimpedance measurement with the help of said stimulation electrodes;
 wherein said electrodes are complemented with at least two impedance reference electrodes suited for placing in contact with the healthy skin surrounding the wound area, and a bioadhesive affinity layer surrounding the stimulation electrodes.

According to an example, in the method, the frame like counter-electrode is used as an anode electrode and the stimulation electrodes are used as cathode electrodes, or vice versa. According to an example, in the method, the electrodes are suited for bioimpedance measurement with measurement frequencies in the range of 10 Hz-200 000 Hz, According to an example, in the range of 1 000 Hz-50 000 Hz.

Furthermore, the objects of the invention are achieved by a wound dressing comprising at least two impedance reference electrodes, a frame like counter-electrode and stimulation electrodes in a form of an array; and a bioadhesive affinity layer surrounding the stimulation electrodes; said wound dressing being suited for applying on top of the wound so that the stimulation electrode array is on the wound area, and that the at least two impedance reference electrodes and the frame like counter-electrode are suited for placing in contact with the healthy skin surrounding the wound area; which electrodes are suited for applying LIDC type electrical stimulation current to the wound area and for bioimpedance measurement.

According to an example, the frame like counter-electrode is anode electrode and the stimulation electrodes are cathode electrodes, or vice versa. According to an example, the electrodes are suited for bioimpedance measurement with measurement frequencies in the range of 10 Hz-200 000 Hz, According to an example, in the range of 1 000 Hz-50 000 Hz.

According to an example, the polarity of the frame like counter-electrode and the stimulation electrodes is switchable. According to an example, the wound dressing has a button battery, a printed battery structure or an electrochemical cell used as a power source for the electrodes.

According to an example, the wound dressing has a tether with the electrical connections of the electrodes. More According to an example, the tether has a tether connector connectable to an electrode routing plug of an outside measurement terminal device and/or to an external power source. According to an example, the wound dressing is produced by reel-to-reel print manufacturing, by sheet print manufacturing, by rotary screen print manufacturing or by any other mass production print manufacturing.

According to an example, the electrodes and the conductor pattern are printed to a paper substrate, to a polymer substrate or to a composite substrate functioning as a body of the wound dressing. Alternatively, the electrodes and the conductor pattern are etched on top of a suitable layer of plastic laminate, metal laminate or a composite laminate and the etched laminate layer is attached to a paper substrate, polymer substrate or composite substrate functioning as a body of the wound dressing.

According to an example, the bioadhesive affinity layer is manufactured of a peptide modified polysaccharide bioadhesive comprising a peptide component and a polysaccharide component. More According to an example, the peptide component is an integrin binding peptide, such as Arg-Gly-Asp (RGD), Gly-Arg-Gly-Asp-Ser (GRGDS), or cyclic RGD.

According to an example, the polysaccharide component is galactoglucomannan, xyloglucan or galactomannan. Alternatively, the polysaccharide component is spruce galactoglucomannan. According to an example, the polysaccharide component comprises galactose side units. According to an example, surface modification is applied to the wound dressing.

According to an example, the wound dressing comprises a bioactive layer. More According to an example, the bioactive layer contains a biopolymer based bioactive glass granules or spheres containing screen printable paste. More According to an example, said screen printable paste contains polylactic acid (PLA) as the polymer component and 20-100 µm granules of an antimicrobial angiogenesis-promoting bioactive glass, e.g. BAG-S53P4. According to an example, antibacterial silver is applied to the wound dressing. According to an example, the wound dressing is used for facilitating wound healing.

DETAILED DESCRIPTION OF THE INVENTION

Figure 1:
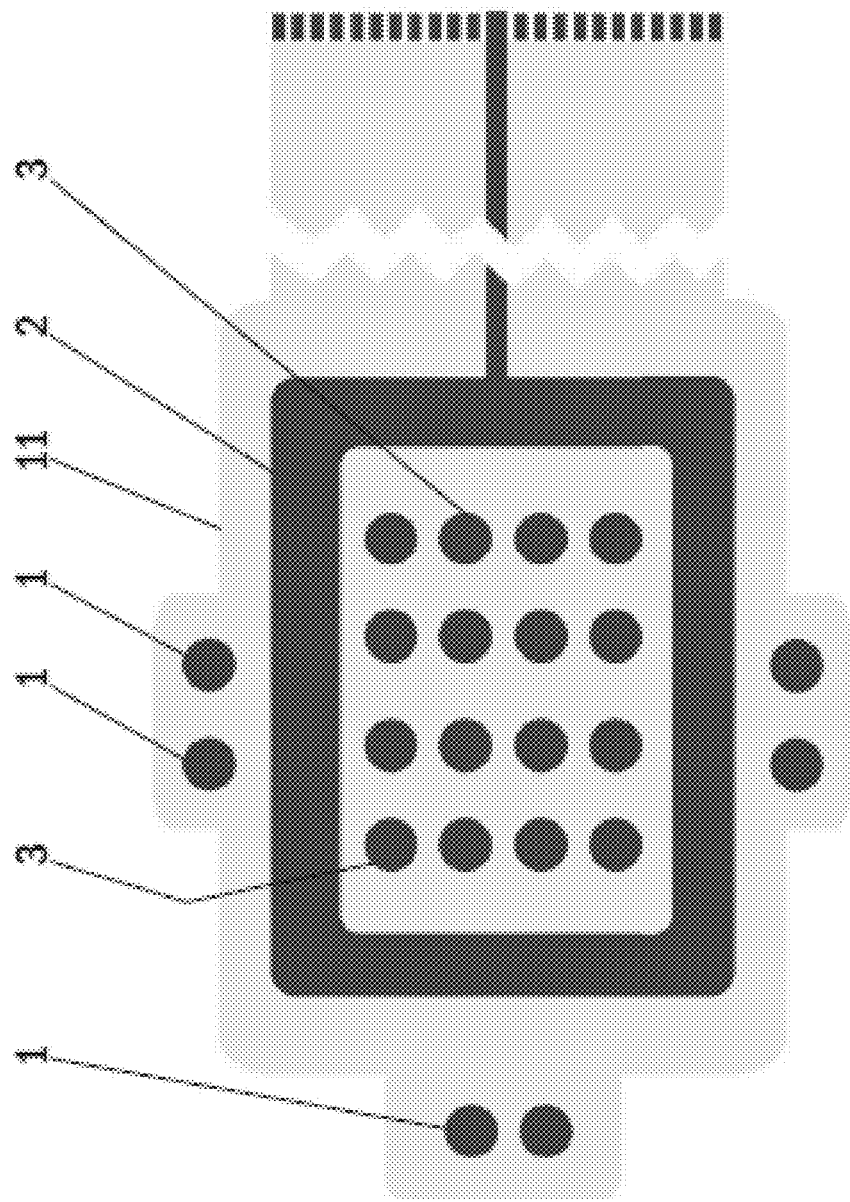
FIG. 1 shows a bottom side view of an electrode arrangement of one embodiment of a wound dressing according to an embodiment of the present invention.

FIG. 1 shows a bottom side view of an electrode arrangement of one embodiment of a wound dressing according to an embodiment of the present invention. The wound dressing according to an embodiment of the present invention comprises a printed substrate 11 having impedance reference electrodes 1, a frame like counter electrode 2 and stimulation electrodes 3 in a form of an array printed on the printed substrate 11. Highly conductive screen printable inks may be used as the material for the electrodes 1-3. The electrodes 1-3 and the conductor pattern may be printed directly to a paper substrate 11, polymer substrate 11 or composite substrate 11 functioning as the wound dressing laminate. Another alternative is to etch the electrodes 1-3 and the conductor pattern on top of a suitable layer of plastic laminate 11, metal laminate 11 or a composite laminate 11 and attach this etched laminate layer 11 to a paper substrate, polymer substrate or composite substrate functioning as the wound dressing laminate. ly, this part may be provided in any size and shape.

Figure 2:
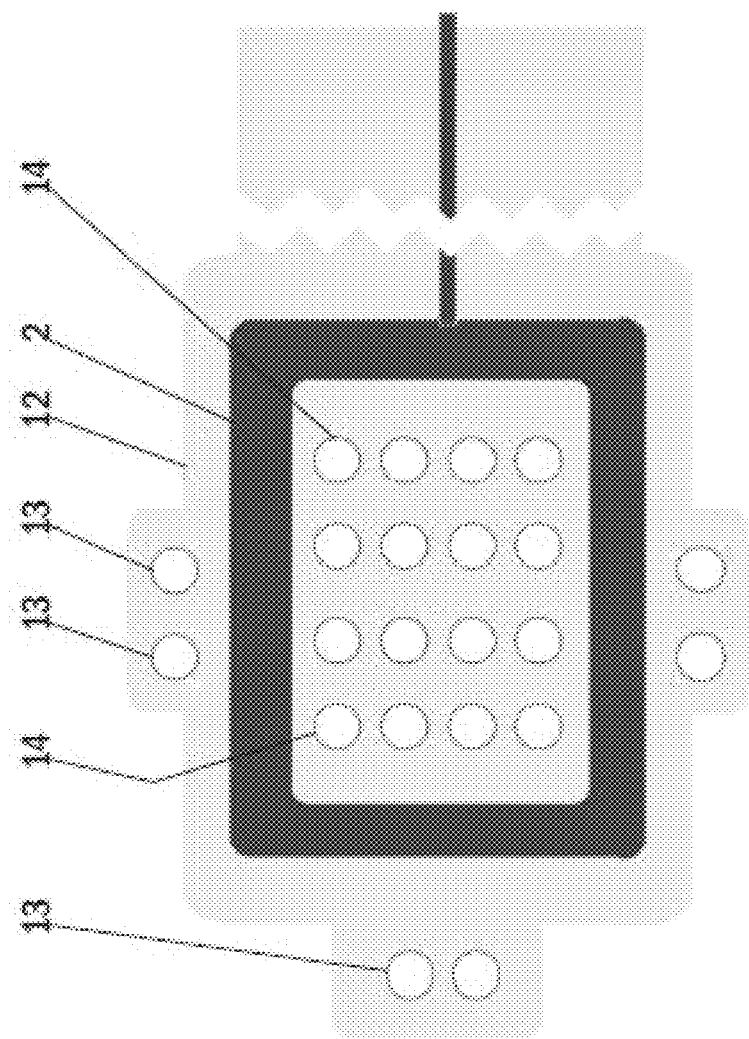
FIG. 2 shows a bottom side view of a lower laminate part of an electrode arrangement of one embodiment of a wound dressing according to an embodiment of the present invention.

FIG. 2 shows a bottom side view of a lower laminate part of an electrode arrangement of one embodiment of a wound dressing according to an embodiment of the present invention. The lower laminate part 12 of an electrode arrangement of a wound dressing according to an embodiment of the present invention contains a printed or etched frame like counter electrode 2 and a number of perforations 13, 14 to allow for wound contact with the stimulation electrode array and impedance reference electrodes. Highly conductive screen printable inks may be used as the material for the frame like electrode 2. The electrode 2 and the conductor pattern may be printed directly to a paper substrate 12, polymer substrate 12 or composite substrate 12 functioning as the lower part of the wound dressing laminate. Another alternative is to etch the electrode 2 and the conductor pattern on top of a suitable layer of plastic laminate 12, metal laminate 12 or a composite laminate 12 and attach this etched laminate layer 12 to a paper substrate, polymer substrate or composite substrate functioning as the lower part of the wound dressing laminate. ly, this part may be provided in any size and shape.

Figure 3:
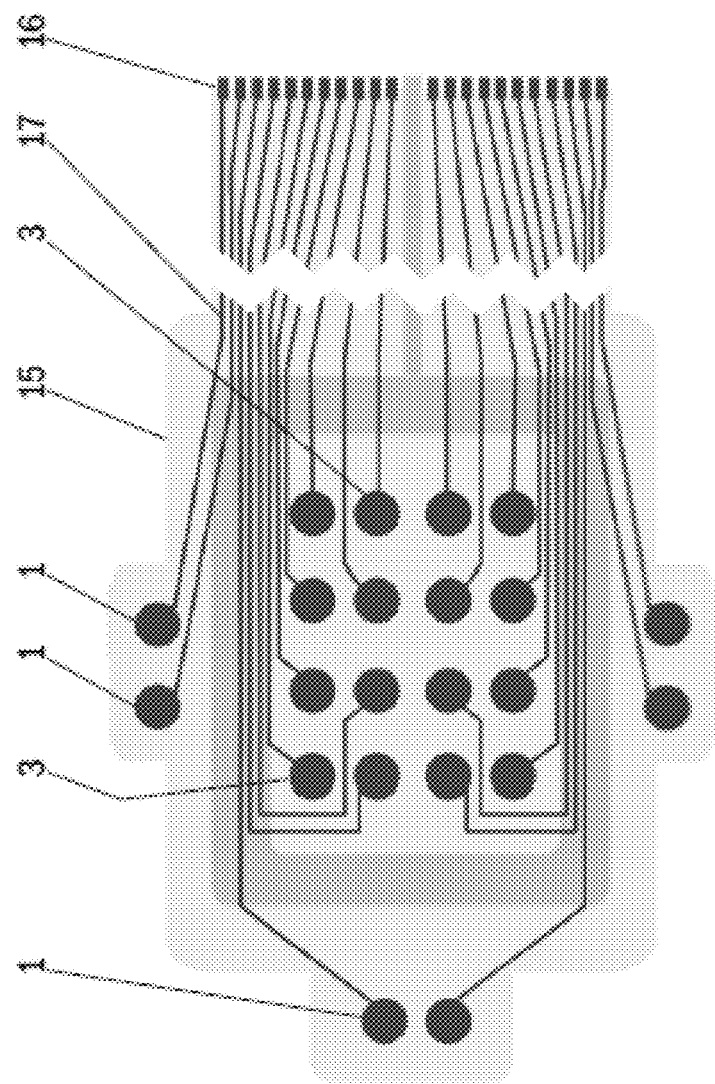
FIG. 3 shows a bottom side view of an upper laminate part of an electrode arrangement of one embodiment of a wound dressing according to an embodiment of the present invention.

FIG. 3 shows a bottom side view of an upper laminate part of an electrode arrangement of one embodiment of a wound dressing according to an embodiment of the present invention. The upper laminate part 15 of an electrode arrangement of a wound dressing according to an embodiment of the present invention contains a printed or etched substrate 15 having impedance reference electrodes 1 and stimulation electrodes 3 in a form of an array printed or etched on the substrate 15. The upper laminate part 15 shown in the FIG. 3 also contains printed connectors 16 and wiring layout 17. Highly conductive screen printable inks may be used as the material for the reference electrodes 1 and the stimulation electrodes 3. The electrodes and the conductor pattern may be printed directly to a paper substrate 15, polymer substrate 15 or composite substrate 15 functioning as a body of the wound dressing.

Another alternative is to etch the electrode array and the conductor pattern on top of a suitable layer of plastic laminate 15, metal laminate 15 or a composite laminate 15 and attach this etched laminate layer 15 to a paper substrate, polymer substrate or composite substrate functioning as the upper part of the wound dressing laminate. The stimulation electrode array 3 may comprise any desired number of electrodes in any desired configuration. A typical non-limiting electrode array comprises 10 to 200 electrodes. The number of arrayed electrodes depends, at least party, from the size and the shape of the wound dressing. The wound dressing may be provided in any sizes and shapes.

Figure 4:
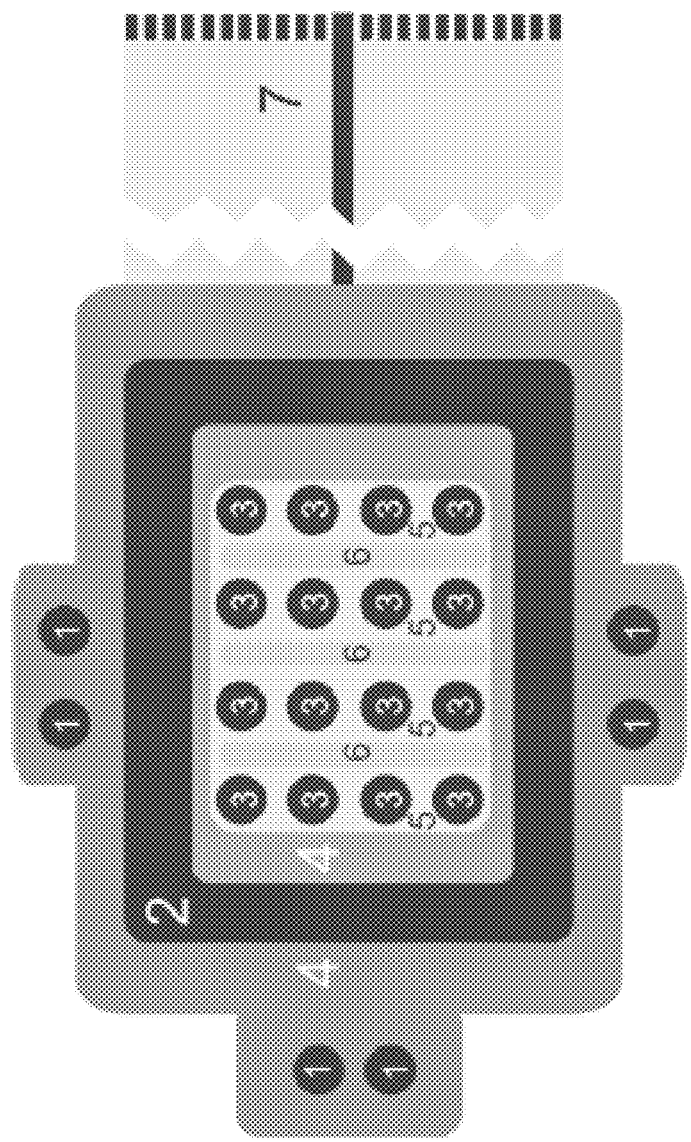
FIG. 4 shows a bottom side view of one embodiment of a wound dressing according to an embodiment of the present invention.

FIG. 4 shows a bottom side view of one embodiment of a wound dressing according to an embodiment of the present invention. The wound dressing according to an embodiment of the present invention contains impedance reference electrodes 1, a frame-like counter electrode 2, a stimulation electrode array 3, a hydrogel adhesive layer 4, a bioadhesive affinity layer 5, a bioactive layer 6 and a tether with a tether connector 7 connectable to an electrode routing plug of an outside measurement terminal device. Impedance reference electrodes 1 provide the reference value for the wound impedance measurement. The frame-like electrode 2 acts as the counter electrode and the stimulation electrode array 3 provides the stimulation current during LIDC stimulation. When mapping the wound various combinations of electrode pairs of the stimulation electrode array 3 can be measured.

When assessing swelling and/or onset of infection the four corner electrodes of the stimulation electrode array 3 can be used. The hydrogel adhesive layer 4 is coated with a suitable non-conductive hydrogel acting as an adhesive. The bioadhesive affinity layer 5 is coated with a peptide modified polysaccharide bioadhesive to be used in the bioadhesive affinity layer 5 and comprises a peptide component and a polysaccharide component. According to an example, the peptide component is an integrin binding peptide, such as Arg-Gly-Asp (RGD), Gly-Arg-Gly-Asp-Ser (GRGDS), or cyclic RGD. The peptide component provides bioadhesive and hemostatic properties to the present wound dressing, at least partly, owing to its ability to enhance endothelial cell adhesion and proliferation. A number of different polysaccharides having high affinity for cellulosic surfaces may be used as the polysaccharide component in the peptide modified polysaccharide bioadhesive to be used in the bioadhesive affinity layer 5. According to an example, the polysaccharide component comprises galactose side units. A non-limiting example of suitable polysaccharide species is galactoglucomannan, the major hemicellulose type or heteropolysaccharide in softwoods. In one particular embodiment, the polysaccharide component is spruce galactoglucomannan. Other non-limiting examples of suitable polysaccharide species include xyloglucan and galactomannan.

The peptide modified polysaccharide bioadhesive may be produced by activation of the galactose side units in the selected polysaccharide through chemo-enzymatic processes in water medium. Next, the peptides are anchored to these activated sites by peptide coupling while maintaining the integrity of the polysaccharide main chain and hence the affinity towards a cellulosic surface of the wound dressing. Alternative materials for the bioadhesive affinity layer 5 include chitosan and derivatives thereof.

The bioactive layer 6 in FIG. 4 contains a biopolymer based bioactive glass granules or spheres containing paste. This screen printable paste may contain polylactic acid (PLA) as the polymer component and 20-100 μm granules of an antimicrobial angiogenesis-promoting bioactive glass, e.g. BAGS53P4. The electrode routing plug may be integrated directly to the measurement device, or a communication tether may be used in between. The length of the tether of the wound dressing according to an embodiment of the present invention may be very short (in the range of centimeters) or very long (in the range of meters) or something in between. As a power source for the wound dressing according to an embodiment of the present invention a button battery or a printed battery structure, realized either as a hybrid (zinc/air or aluminium/air) or as fully chemical (zinc/silver oxide) battery may be used. Also an electrochemical cell e.g. using enzyme catalyst may be used as a power source for the wound dressing according to an embodiment of the present invention. One such electrochemical cell using enzyme catalyst has been described in an International patent application WO 2007/147942. Hence, the tether connector is providing contact to the power supply containing connector during stimulation and to the bioimpedance measuring device during evaluation of degree of wound healing.

The principal idea of application of the wound dressing according to an embodiment of the present invention is that the wound dressing is applied on top of the wound so that the stimulation electrode array 3 is on the wound area and the frame like counter-electrode 2 is on and in contact with the intact skin surrounding the wound area. The frame like counter-electrode 2 may e.g. be square formed. The stimulation electrode array 3 may e.g. be a simulation software optimized stimulation electrode array 3.

The injured tissue is normally characterized by a higher potential compared with the surrounding intact skin and in the wound edge cells are in electric field. Electrical stimulation according to an embodiment of the present invention restarts or accelerates wound healing process by imitating the natural electrical current and to increase this lateral current, positive polarity should be placed on the wound and negative on the intact skin area. The polarity of the wound may also be reversible. When applying electrical stimulation to the wound the current density should be sufficiently high in the wound and the electrode layout should be selected such that the current reaches the deeper skin layers. As electrical stimulation is applied to the wound there is regenerated epithelium and granulation tissue being formed under the wound stimulation points this will increase the local contact resistance between the stimulation electrode and the wound. This causes the stimulation current to seek to wound stimulation points where the healing is slower this resulting to a more even stimulation effect. Thus, the present wound dressing may be termed as self-adjustable.

In the wound dressing according to an embodiment of the present invention point-like stimulation electrodes of the stimulation electrode array 3 on the wound surface provide a better skin contact to the wound when compared to larger structures due to more flexible surface of the wound dressing. The electrode placement according to an embodiment of the present invention also provides better current density feature and additionally gives possibility to self-regulatory adjustment of the wound stimulation current as the impedance increases at the edges of the wound as the healing proceeds and the stimulation current naturally seeks lower impedance pathway. This electrode placement also offers a possibility to polarity reversal. The polarity of the frame like counter-electrode 2 and the stimulation electrodes 3 is switchable during treatment to enhance the diffusion of various wound healing related components and decrease the formation of concentration gradients. The electrodes 2, 3 can also be multiplexed so as to allow for measurement of bioimpedance in a two electrode and four electrode configurations.

The wound dressing structure according to an embodiment of the present invention is flexible and thin and the wound dressing surface area is scalable. The proposed wound dressing is self-sustaining and does not involve leads during stimulation functionality, thereby providing overall convenience and ease of use for the patient. The wound dressing structure according to an embodiment of the present invention may be manufactured by using reel-to-reel print manufacturing. At least the electrodes and potentially an integrated power source in the wound dressing may be produced by reel-to-reel print manufacturing. Also a surface modification may be applied to the wound dressing in order to enhance the wound contact for example by drop casting, by curtain spraying or by administration of skin adhesive using spraying techniques.

In some embodiments, antibacterial silver may be used in the wound dressing surface facing the wound; this improving the antimicrobial properties against wound infection. Furthermore, bioactive glass may be used in the wound dressing surface facing the wound as bioactive glass possesses good antimicrobial properties. The use of bioactive glass may provide additional protection against wound infection or reduce the on-going infection. Moreover, bioactive glasses enhance angiogenesis, or blood vessel growth, a process that is critical in wound healing. Suitable bioactive glasses are readily available and easily chosen by a person skilled in the art.

One of the signs of a wound infection is an increase in body temperature around the wound area. Thus, if desired, a built-in thermometer or thermocouple can be included in the present wound dressing to allow early detection and monitoring of a possible wound infection.

The wound dressing according to an embodiment of the present invention incorporates galvanic wound stimulation functions with a wound healing monitoring possibility by using bioimpedance method. The measurement of bioimpedance is non-intrusive and do not require removal of the wound dressing, therefore it may be used in less controlled environment such as in home care.

The bioimpedance monitoring of wound healing is based on the impedance measurement of wound tissue in reference to intact skin. Three most common electrode systems include 2-, 3- and 4-electrode systems. In one embodiment of an embodiment of the present invention the wound healing monitoring is performed by utilizing 2-electrode bioimpedance measurement configuration. In the 2-electrode bioimpedance measurement configuration the same electrodes are used for both the excitation current feeding and voltage measurement. The output of 2-electrode bioimpedance measurement consists of the electrode impedance of both electrodes, the skin impedance under both electrodes and the tissue impedance between the two measurement electrodes. The outer layers of skin provide very high impedance compared to underlying tissues. Therefore, the strongest indication of wound healing can be obtained when the impedance of various skin layers is included in the measurements. The 2-electrode bioimpedance measurement method outputs so called true impedance since negative sensitivity areas do not exist in this configuration. This makes the analysis of the measurement results less prone to misinterpretations.

Skin impedance can also be measured using the 3-electrode bioimpedance measurement configuration; however this includes certain obvious disadvantages. The 3-electrode bioimpedance measurement includes areas of negative sensitivity, which may compromise correct interpretation of the output. Placing of the third electrode allows for obtaining reliable and comparable results; this may also prove to be difficult and impractical in clinical use.

With the help of this structure the wound dressing according to an embodiment of the present invention may generate and repair the biomimicking potential difference between the wound area and the surrounding intact skin. The wound dressing according to an embodiment of the present invention may deliver a micro-amperage DC stimulus current to the wound tissue. The wound dressing according to an embodiment of the present invention may be used alongside with the conventional wound care practices. The stimulus current may be limited by either separately printed resistors, internal resistance of the battery or possibly only by the skin/tissue impedance, so that the treatment current is self-regulated. The stimulus current may be fed to the wound surface through multiple antibacterial silver pathways; this improving the electrode-skin contact.

A wound healing process usually starts from the edges of the wound and the wound base lifts up. The skin integrity is gradually regained and the amount of exudates is reduced in the peripheral wound area. Consequently, the impedance increases, and more current flows to the open and moist centre of the wound which provides a lower impedance pathway. In the use of the wound dressing according to an embodiment of the present invention the stimulation current penetrates the skin surface and enters to the underlying wound tissue, thus improving the healing impact.

The bioimpedance measurements may be carried out using at least one frequency depending on the width and the depth of the wound. Measurement frequencies in the range of 10 Hz-200 000 Hz and According to an example, in the range of 1 000 Hz-50 000 Hz may be used. The bioimpedance measurement of the wound dressing according to an embodiment of the present invention may be based on a stand-alone-device and connected to the wound dressing 12 only for the time of measurement.

Due to the electrical simplicity of the wound dressing, a communication tether is to be used between the outside measurement terminal device and the wound dressing. The tether provides galvanic connection between the outside measurement terminal device and the impedance measurement electrodes on the wound dressing. In a certain embodiment, the patch may contain intelligent electronics, and a wireless communication method, such as e.g. infrared communication method or RF communication method may provide the connection to the measurement device instead.

The impedance measurement device may be a handheld device. The impedance measurement device may have a flat connector probe that is slid into a fold on the patch. Alternatively, the impedance measurement device may have a measurement clip that clamps around a contact extrusion on the patch. Furthermore alternatively, the impedance measurement device may be pressed against contacts on the patch.

In addition to the impedance measurement functionality the outside measurement terminal device may contain means to display the result immediately to the operator, store the measured data and to upload the data to the operator's personal computer. As the device may be used in clinical trials, precautions will be taken to make the electrical and physical interfaces of the device safe.

Monitoring the wound healing process through bioimpedance measurements is very precise and sensitive. Even wounds as small as a puncture wound made by a needle are detectable and monitorable by the present arrangement. The same applies to wound types the healing which is particularly challenging to be monitored otherwise, i.e. wounds excreting pus or other fluids.

The present wound dressing may be used to treat any type of wounds, in particular chronic wounds. As used herein, the term "treatment" refers not only to a complete healing of a wound, but also to alleviation and amelioration of symptoms related to incomplete or improper wound healing, including, but not limited to, pain, swelling or edema, burning, itching, rash, redness, discoloration and dry, scaly skin.

Chronic wounds, or ulcers, are wounds or open sores that will not heal or keep returning. Ulcers may develop anywhere on a human body, foot and leg ulcers being the most typical ulcer types. Non-limiting examples of ulcers to be treated in accordance with an embodiment of the present invention include pressure ulcers, or bedsores, venous ulcers, neuropathic (diabetic) ulcers, and arterial (ischemic) ulcers. Typically in foot and leg ulcers, the present wound dressing is to be worn under compression stockings.

Also burn wounds, including first to third degree burns, may be treated with the wound dressing according to an embodiment of the present invention. As the present wound dressing is fully scalable, it may in some extreme embodiments be formulated as a bed sheet to cover large-surface wounds, such as large-surface burn wounds.

The wound dressing according to an embodiment of the present invention and the electrode arrangement for facilitating wound healing according to an embodiment of the present invention provide clear advantages and improvements in the area of the treatment of chronic wounds. The wound dressing according to an embodiment of the present invention and the electrode arrangement for facilitating wound healing according to an embodiment of the present invention provide a continuous, non-invasive and objective solution for monitoring chronic wound healing without disturbing the delicate healing process.

A further advantage of the present wound dressing and the electrode arrangement for facilitating wound healing is easy hygienic disposal with hospital or household waste. This is made possible by using only combustible and/or biodegradable materials in the wound dressing and the electrode arrangement.

Figure 5A:
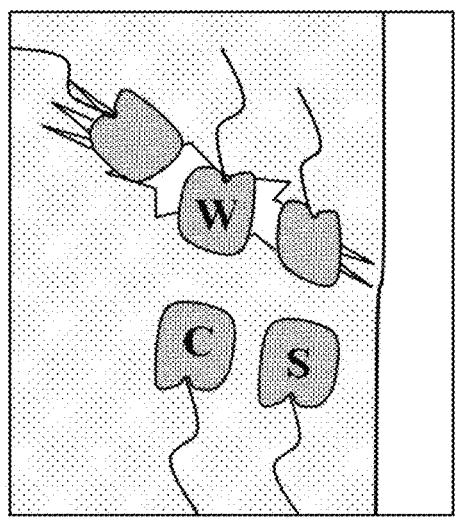
FIG. 5A shows an example of lettered electrodes on and around a wound.
Figure 5B:
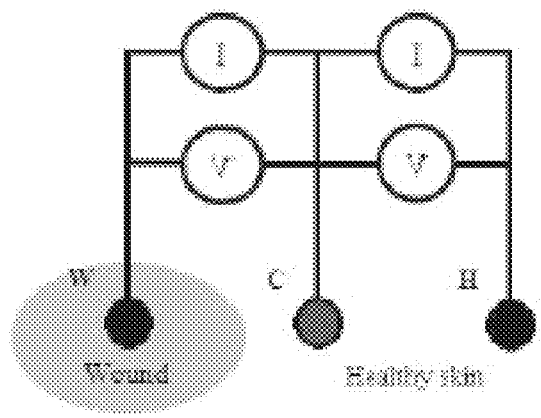
FIG. 5B shows an electrical schematic of the electrode arrangement of FIG. 5A.

FIG. 5A shows a basic example electrode arrangement with an electrode W on a wound, an electrode H on intact skin and an electrode C on intact skin and common to both the wound and reference measurements. FIG. 5B shows an schematic of the arrangement of FIG. 5A.

Figure 6A:
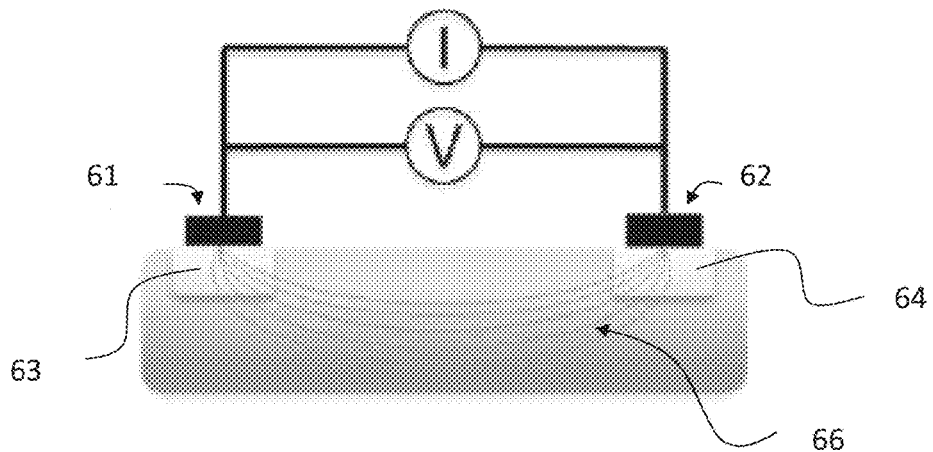
FIG. 6A shows an example effect of a two electrode system on skin.

FIG. 6A shows an illustration of a two-electrode measurement configuration. The configuration has a first electrode 61 and a second electrode 62. Below each electrode is an area 63 and 64 respectively which indicates skin impedance at the area under the electrode. The impedance of areas 63 and 64 can often provide the largest contribution to the total tissue impedance, particularly at low measurement frequencies. The resulting electric field 66 between the two electrodes is shown.

Through such a configuration a measurement output can be determined. The system has a total impedance which is the sum of tissue impedance and the impedance of each electrode 61 and 62.

In such a two electrode system, a single electrode paid can be sued for both excitation current deeding (I) and voltage measurement (V). The output of a two electrode bioimpedance measurement can include the electrode impedance of both electrodes, electrode-ski interface (e.g. any electrode paste or adhesive if any), the skin impedance under both electrodes and the tissue impedance between the two measurement electrodes 61 and 62. Additionally, it has been found that the outer layers of skin typically provide very high impedance compared to underlying tissues.

Wounds typically start to heal from the bottom of a wound. This is often due to the formation of granulation tissue and at the same time the edges of a wound start to close. It is therefore useful to not only monitor the spatial changes of a wound area but also the changes in a wounds lateral direction. It has been found that there are two useful ways to affect measurement depth. One is inter-electrode spacing and the other is measurement frequency.

It has been found that at low measurement frequencies the Stratum Corneum, i.e. the dead cell layer of the epidermis, provides the largest contribution to measured total impedance. The contribution seems to decline as the frequency increases.

In a model where the epidermis is modelled using a parallel combination resistance and capacitance, the dermis and subcutaneous tissues are modelled using a simple resistor. The stratum Corneum of the epidermis can have a very high frequency dependency in comparison to viable skin layers and subcutaneous tissue. At a low measurement frequency the tissue impedance is mainly comprised of the impedance of the epidermis. As the frequency is increased, more current flows through the capacitive element of the epidermis. Parallel combination of the capacitive and resistive elements results in a major decrease in the impedance of the epidermis.

Frequency dependency of the dermis and subcutaneous tissue is much lower. Therefore their relative contribution to the total impedance measured increases as the measurement frequency increases. Appropriate frequency selection can enable monitoring of changes in the electrical properties of different depth tissue layers.

Figure 6B:
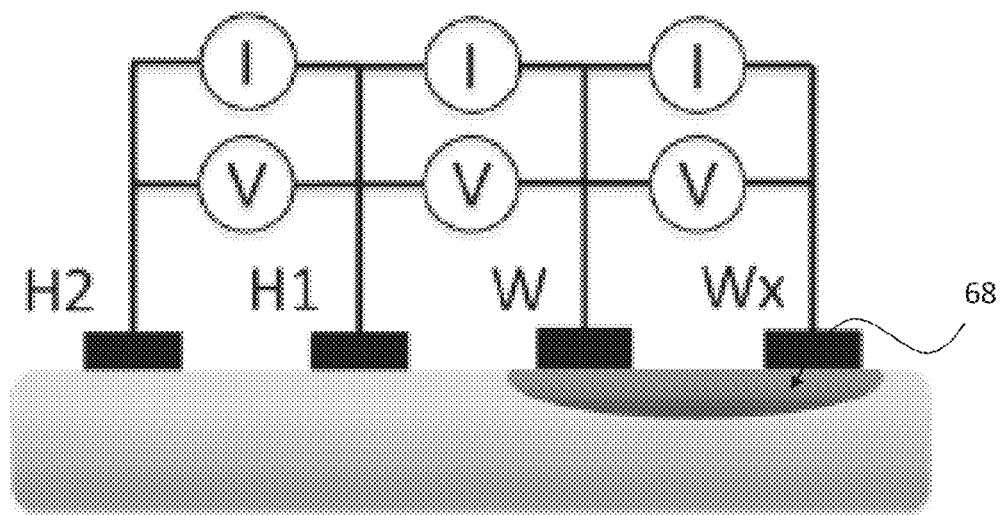
FIG. 6B shows an example effect of a system similar to FIG. 5A on skin.

FIG. 6B shows a similar configuration as in FIGS. 5A and 6A, wherein there are two electrodes H1 & H2 which are on healthy, intact skin and two electrodes W & Wx which are on a wound area 68.

Impedance can be measured in such a configuration between an electrode W and a reference electrode H1. The wound impedance can be referenced to the impedance measured from the intact skin site adjacent to the wound, e.g. H1 & H2. From this a healing ration can be calculated.

Furthermore, impedance from a configuration can be measured with a variety of excitation frequencies using multiple electrodes H & W as shown. The result can be proportioned with the reference measurement taken from H electrodes.

As the wound heals the impedance of the wound will approach the impedance of the surrounding healthy skin and therefore the progress of the healing can be measured.

It is therefore possible to evaluate the status of a wound based on applied two-electrode bioimpedance measurement. A two-electrode configuration represents so a called "true impedance", in which areas of negative sensitivity do not exist unlike in the other basic bioimpedance measurement configurations. In two-electrode measurement the sensitivity is dictated by current density which peaks right under the electrodes and decreases with distance from the electrodes. This makes it easier to place electrodes and interpret the results. Two-electrode configuration can be a good alternative for wound monitoring as measures impedance right under the electrode surface such as skin or wound base, where changes are the largest.

In wound measurement one electrode is placed on the wound and the other on intact skin. The electrode placed on the intact skin is shared by the skin impedance measurement, which is used as a reference. High impedance of the stratum corneum layer of epidermis is volatile and fairly high daily variations can be observed in the impedance of intact skin. The common (H1) electrode binds the wound measurement and reference together. The common electrode creates a baseline in a way that unwanted volatility of skin impedance can be reduced, for example when a wound-skin ratio is calculated. Another advantage of such a setup is that it decreases the possibility of electrical short-circuit through highly conductive ionic wound exudate, which is typical for venous ulcer. To increase the reliability of reference measurement it may be advisable to measure impedance at slightly higher frequencies so that the contribution of volatile stratum corneum layer is reduced and measurement depth is increased.

Results show that indications of healing of the wound can be seen first at higher frequencies. During first days of the follow-up monitoring the largest changes are often at the higher frequencies, while low frequency results do not seem to indicate any significant change.

A downside of the two-electrode configuration is that the measurement results also include the impedance originating from the electrodes and leads. Because of this high and even quality electrodes should be used and the effect of the electrode impedance minimized or controlled. In many cases it is also impossible to make distinction between electrode impedance and tissue impedance. Despite of this the total electrode-impedance can be easily measured by connecting electrodes face-to-face and thus accounted for.

Figure 7:
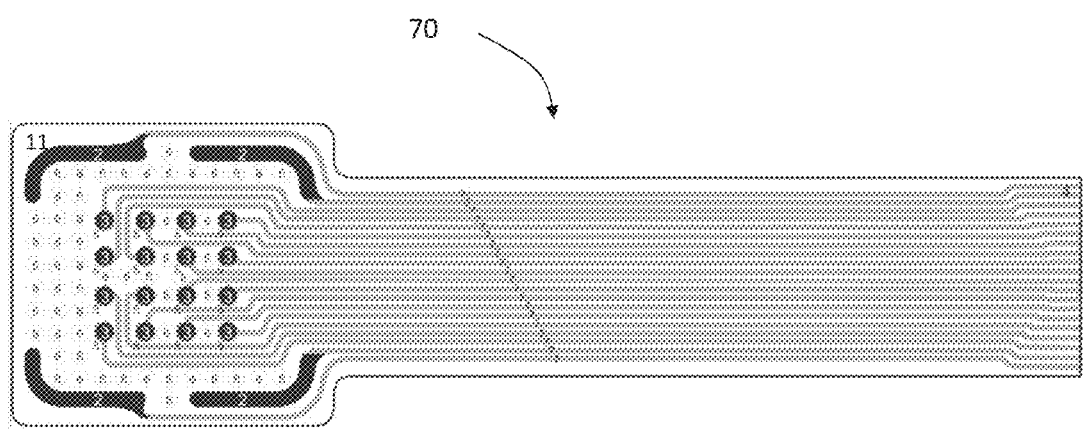
FIG. 7 shows a bottom side view of an electrode arrangement according to an embodiment of the present invention.
Figure 8:
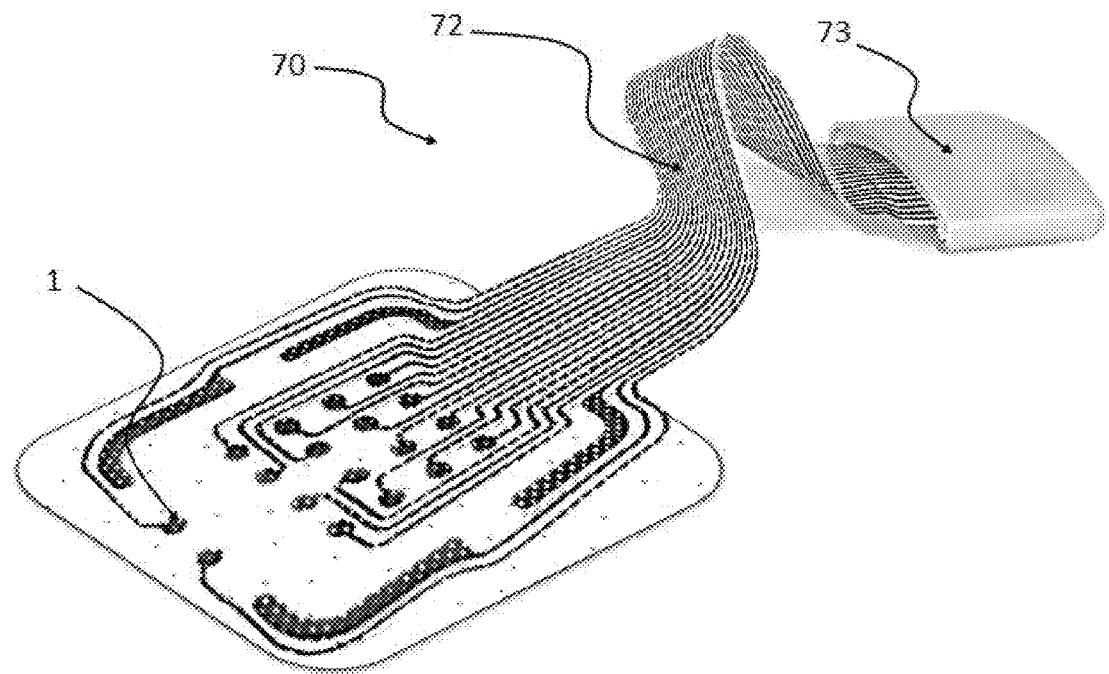
FIG. 8 shows a perspective view of an electrode arrangement and connector according to FIG. 7.
Figure 9:
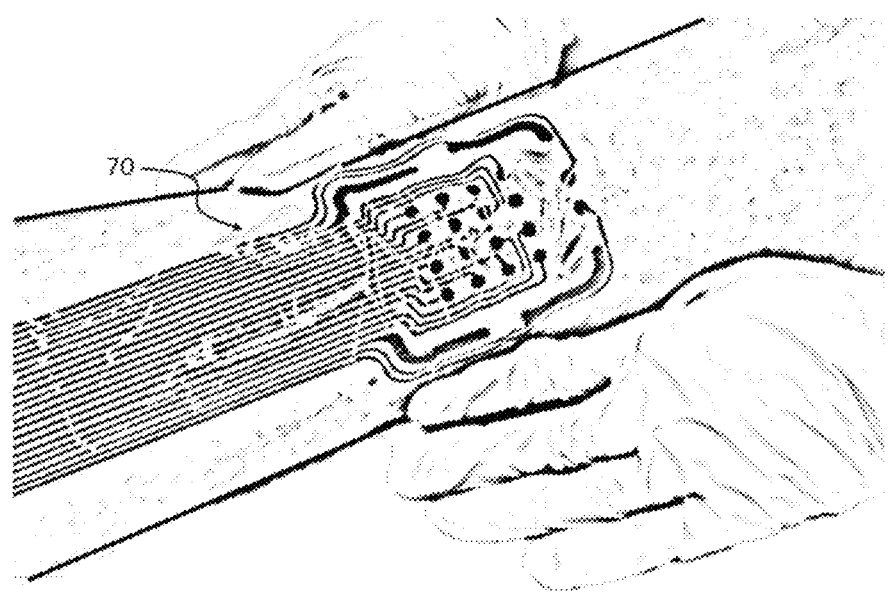
FIG. 9 shows the electrode arrangement of FIG. 8 applied to a wound.

FIG. 7 shows an electrode arrangement 70 similar to those of FIGS. 1-4. The electrode arrangement 70 includes a printed substrate 11, such as a perforated PET substrate. The frame like counter electrodes 2 are arranged in a broken frame arrangement. In place of a single frame like counter electrode 2 in FIGS. 1-4, in the present arrangement there are four frame like counter electrodes 2 which form the corners of a frame of the arrangement. Additional embodiments can include different numbers of frame like counter electrodes 2 which completely or partially surround stimulation electrodes 3. For example, the gaps between two or more of the frame like counter electrodes 2 in FIG. 7 can be closed to form a one or more larger frame like counter electrodes. However, as shown in FIGS. 7-9, four frame like counter electrodes 2 can be used, one for each corner of the arrangement.

These frame like counter electrodes 2 can be in two or more segments and can be utilized both in stimulation mode and in measuring mode and in different ways and combinations. In stimulation mode, each segment 2 can be serially connected to form one single frame acting as a counter electrode for wound stimulation electrodes, e.g. as an anode when the stimulation electrodes are connected as cathodes and vice versa.

In a measuring mode, each segment 2 can be utilized both individually and in a combination with one or more other segments 2. For example, in a reference value assessment phase, bioimpedance can be measured between each of the different segments 2 to obtain a reference values of the intact skin surrounding the wound. In order not to obtain inaccurate values due to measurement of only local skin responses, which can cause large variations, each segment 2 can be sufficiently large and contact the skin in a sufficiently large area to avoid these inaccuracies. This large enough area also allows for easy and accurate identification of measurement errors due to improper skin contact or wetting effects due to exudate short circuiting adjacent electrodes. An example, as can be seen in the FIGS. 7-9 is that the frame like counter electrode segments 2 are each at least twice, and preferably at least five to ten times or more the area of the stimulation electrodes 3.

In a wound mapping phase, each segment 2 can act as a counter electrode for each of the stimulation/measurement electrodes 3 in the array during bioimpedance measurement. This provides information of the wound area directly under each of the stimulation/measurement electrodes 3.

The bioimpedance can be measured at each location and at a number of different frequencies and the combination of the responses can provide comprehensive tissue specific information. Measured bioimpedance responses can then be related against obtained intact skin reference value(s) to estimate the degree of healing at each electrode point 3 in the array.

The arrangement 70 can also include bioadhesive affinity layers 5, though not mandatory, as well as bioactive dots 6. The optional bioadhesive affinity layer 5 surrounding each of the electrodes 3 in the array can be a conducting gel providing a weak adhesive effect against the bottom of the wound. The arrangement 70 can also include a tether connector 72 to an electrode routing adapter 73 as shown in FIG. 8. FIG. 9 shows the arrangement 70 applied to a wound. Furthermore, FIGS. 8 and 9 show two impedance reference electrodes 1 arranged outside the array of stimulation electrodes 3.

It will be obvious to a person skilled in the art that, as the technology advances, the inventive concept can be implemented in various ways. The invention and its embodiments are not limited to the examples described above but may vary within the scope of the claims.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A wound dressing comprising:
   stimulation electrodes arranged in an array, said array of stimulation electrodes capable of providing low intensity direct current (LIDC) type electrical stimulation current to a wound area,
   at least two impedance reference electrodes arranged outside said array of stimulation electrodes, and
   at least one frame-like counter-electrode arranged outside said array of stimulation electrodes,
   wherein the frame-like counter-electrode extends contiguously in a parallel direction to the stimulation electrodes at adjacent sides of the stimulation electrode array.

2. The wound dressing according to claim 1, wherein the stimulation electrodes, impedance reference electrodes and at least one frame-like counter electrode are arranged on a printed substrate.

3. The wound dressing according to claim 1, further comprising at least two frame-like counter electrodes, wherein at least one of the frame like counter electrodes forms a corner around the array of stimulation electrodes.

4. The wound dressing according to claim 1, further comprising a bioadhesive affinity layer surrounding the stimulation electrodes.

5. The wound dressing according to claim 2, wherein said wound dressing is capable of being applied on top of a wound so that the stimulation electrode array can be on a wound area while the at least two impedance reference electrodes and the frame-like counter-electrode can be placed in contact with healthy skin surrounding the wound area.

6. The wound dressing according to claim 1, wherein the stimulation electrodes and frame-like counter-electrode(s) are capable of bioimpedance measurement with measurement frequencies in the range of 10 Hz-200 000 Hz.

7. The wound dressing according to claim 1, wherein a polarity of the frame-like counter-electrode(s) and the stimulation electrodes is switchable.

8. The wound dressing according to claim 1, further comprising a button battery, a printed battery structure or an electrochemical cell used as a power source for the stimulation electrodes and frame-like counter-electrode(s).

9. The wound dressing according to claim 1, further comprising a tether with the electrical connections of the stimulation electrodes and frame-like counter-electrode(s).

10. The wound dressing according to claim 4, wherein the bioadhesive affinity layer includes a peptide modified polysaccharide bioadhesive having a peptide component and a polysaccharide component.

11. The wound dressing according to claim 1, further comprising a bioactive layer containing a biopolymer based bioactive glass granules or spheres containing screen printable paste.

12. The wound dressing according to claim 1, wherein the stimulation electrodes and frame-like counter-electrode(s) are multiplexed.

13. A method for measuring wound healing when providing low intensity direct current (LIDC) type electrical stimulation current to a wound area with the aid of stimulation electrodes in a form of an array, said method comprising the steps of:

performing bioimpedance measurement with at least one frame-like counter-electrode arranged outside an array of stimulation electrodes and with said array of stimulation electrodes;

wherein said stimulation electrodes and frame-like counter-electrode(s) are complemented with at least two impedance reference electrodes arranged outside said array of stimulation electrodes and arranged suitably for placing in contact with healthy skin surrounding a wound area, and wherein the frame-like counter-electrode extends contiguously in a parallel direction to the stimulation electrodes at adjacent sides of the stimulation electrode array.

14. The method according to claim 13, wherein the stimulation electrodes and frame-like counter-electrode(s) are suited for bioimpedance measurement with measurement frequencies in the range of 10 Hz-200 000 Hz.

* * * * *